United States Patent
Bornzin

(10) Patent No.: US 6,832,112 B1
(45) Date of Patent: Dec. 14, 2004

(54) METHOD OF ADJUSTING AN AV AND/OR PV DELAY TO IMPROVE HEMODYNAMICS AND CORRESPONDING IMPLANTABLE STIMULATION DEVICE

(75) Inventor: Gene A. Bornzin, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 439 days.

(21) Appl. No.: 10/035,744

(22) Filed: Dec. 28, 2001

(51) Int. Cl.⁷ .............................................. A61N 1/365
(52) U.S. Cl. ........................................................ 607/9
(58) Field of Search .......................... 607/1, 9, 26, 27, 607/28, 123

(56) References Cited

U.S. PATENT DOCUMENTS

| | | |
|---|---|---|
| 4,686,988 A | 8/1987 | Sholder ................. 128/419 PT |
| 4,708,142 A | 11/1987 | DeCote, Jr. ............ 128/419 PT |
| 4,712,555 A | 12/1987 | Thornander et al. ... 128/419 PG |
| 4,729,376 A | 3/1988 | DeCote, Jr. ............ 128/419 PT |
| 4,788,980 A | 12/1988 | Mann et al. ........... 128/419 PG |
| 4,809,697 A | 3/1989 | Causey, III et al. ... 128/419 PT |
| 4,940,052 A | 7/1990 | Mann et al. ........... 128/419 PG |
| 4,944,298 A | 7/1990 | Sholder ................. 128/419 PG |
| 4,944,299 A | 7/1990 | Silvian ................. 128/419 PG |
| 4,969,467 A | 11/1990 | Callaghan et al. ..... 128/419 PG |
| 5,350,410 A | 9/1994 | Kleks et al. ................... 607/28 |
| 5,466,254 A | 11/1995 | Helland ....................... 607/123 |
| 5,534,016 A | 7/1996 | Boute ............................. 607/9 |
| 5,573,550 A | 11/1996 | Zadeh et al. ................... 607/28 |
| 5,685,315 A | 11/1997 | McClure et al. ............. 128/708 |
| 6,498,950 B1 * | 12/2002 | Bradley ........................ 607/27 |

* cited by examiner

Primary Examiner—George Manuel

(57) ABSTRACT

Methods and apparatus are provided for adjusting the AV/PV delay of an implantable stimulation device so as to achieve fusion of an externally provided ventricular stimulus with the patient's own intrinsic depolarization.

37 Claims, 9 Drawing Sheets

METHOD OF ADJUSTING AN AV AND/OR PV DELAY TO IMPROVE HEMODYNAMICS AND CORRESPONDING IMPLANTABLE STIMULATION DEVICE

FIELD OF THE INVENTION

The present invention relates to implantable stimulation devices and more particularly to implantable pacemakers that automatically adjust their AV delay and/or PV delay (i.e., interchamber delay) to improve hemodynamics. The invention also relates to methods of adjusting an AV delay and/or a PV delay.

BACKGROUND OF THE INVENTION

The heart is a four-chamber pump composed of two atria and two ventricles. The atria function principally as entryways to the ventricles, but they also pump weakly to help move the blood on through the atria into the ventricles. The ventricles supply the main force that propels the blood through the lungs and through the peripheral circulatory system.

At an appropriate time, which is determined by a sinoatrial or "SA" node, an a periodic spontaneous electrical depolarization is provided which causes the muscle tissue surrounding the atrium to depolarize. Depolarization of the atrial muscle tissue can be monitored by detecting an electrical signal reflective of atrial depolarization known as a P-wave.

Subsequent to the occurrence of the P-wave, the atrial muscle contracts and forces blood from the atrium into the ventricle. The SA node stimulus that caused the atrium to depolarize also travels to the ventricle and the atrioventricular or "AV" node through the AV bundle.

The AV node is neuromuscular heart tissue in the lower middle part of the right atrium. It receives the impulse to contract from the SA node, via the AV bundle, and transmits the impulse through a Purkinje bundle of pathways to the ventricles. The Purkinje bundle is composed of neuromuscular heart fibers that pass from the AV node forward to the septum between the ventricles, where it divides into right and left bundle branches, one for each ventricle. The fibers thus transmit the SA node stimulus from the atria to the ventricles.

As the SA node stimulus travels through the heart, it is typically delayed by the AV node by an amount that corresponds to the time it takes the blood to flow from the atrium to the ventricle. After the delay (natural conduction time of the heart), the conducted depolarization arrives at the ventricular muscle tissue, which causes the ventricular muscle tissue to depolarize.

Depolarization of the ventricular muscle tissue is manifest in the occurrence of an electrical signal known as the QRS-wave complex, which shows the depolarization of the muscle tissue along the heart's septum. For simplicity, one may easily use the largest amplitude signal from the QRS wave complex to monitor the occurrence of the QRS signal. This major signal, which relates to the major septum depolarization, is the "R" wave.

Immediately following this depolarization, the ventricular muscle tissue contracts and forces the blood through arteries to various body locations. The ventricular muscle tissue then re-polarizes and begins to relax. Immediately prior to ventricular re-polarization and relaxation an electrical signal may be sensed in the ventricular muscle tissue, known as the "T" wave.

In this manner, the heart pumps blood by having the atria contract at a rate determined by the SA node, and after the natural conduction time, by having the ventricles contract. After a period of time, when the atrium has refilled with blood returning from throughout the body, the process repeats.

The process wherein the atria and ventricles sequentially depolarize and contract in order to pump blood and get ready to depolarize again, is called the cardiac cycle. A given cardiac cycle thus includes one P-wave (or equivalent atrial activity evidencing depolarization of the atria), one QRS-wave (or equivalent ventricular activity evidencing depolarization of the ventricles) and one T-wave (or equivalent ventricular activity evidencing re-polarization of the ventricles).

An implantable stimulation device is an implantable medical device that monitors the activity of the heart for the occurrence of P-waves and/or QRS-waves, and steps in with electronically generated stimuli, when needed, to force the depolarization of the atria and/or ventricles.

A generated stimulus that is delivered to the atrium from an implantable stimulation device is referred to as an A-pulse. A stimulus that is delivered to the ventricle is referred to as a V-pulse. Most implantable simulation devices are configured to provide an A-pulse and/or V-pulse only if a prescribed period of time has elapsed without the occurrence of a P-wave and/or an R-wave, i.e., without the occurrence of natural heartbeats.

The period of time between depolarization of the atrium and depolarization of the ventricle is referred to as the PQ or PR interval. For most dual-chamber implantable stimulation device modes of operation, the device will only generate an A-pulse at the conclusion of an atrial escape interval, and only if a P-wave does not occur during the interval.

The length of time (which is programmable in most implantable stimulation devices) between an atrial paced event, and the delivery of a ventricular output pulse, is referred to as the AV delay or AV interval. An AV delay may be terminated, i.e., a ventricular pulse will not be delivered to the heart's ventricle by the implantable stimulation device, if an intrinsic ventricular event, an R wave, is sensed before the AV delay times out.

The PV delay or PV interval is the time period from the onset of the intrinsic P wave (atrial depolarizaton) to the ventricular pacing stimulus. The AV delay and the PV delay are measured in milliseconds. An implantable stimulation device, for most modes of operation generates a V-pulse only if the PV delay elapses after atrial activity without the occurrence of an R-wave. The heart is thus afforded as much time as practical to beat on its own before the electronically-generated stimuli of the pacemaker are delivered to the heart, causing the ventricle to contract.

In the prior art, when an Implantable stimulation device is implanted in a patient, or thereafter, the value of the AV delay and/or PV delay can be set to a value that is selected to optimally assist the patient's heart as it performs its critical function of a pump. For many patients, such an AV/PV delay value is a value that is somewhat longer than the natural conduction time of the heart. This affords the patient's heart as long a time period as possible before delivering a stimulation pulse.

However, for other patients, it may be desirable to set the AV delay for the implantable stimulation device at a value that is less than the natural conduction time of the heart, thereby assuring that a V-pulse is preemptively generated with most every cardiac cycle.

While the AV/PV delay of a pacemaker can be programmably set to a desired value, the natural conduction time of the patient may vary, either with time, or with the medical or physiological condition of the patient. For example, the natural conduction time may vary as a function of whether the patient is undergoing physiological stress (e.g., exercise), or whether the patient is under the influence of medication.

In most instances, it would be desirable to have the AV/PV delay of an implantable stimulation device closely mimic the natural conduction time of the heart, because such natural conduction time represents the natural timing between depolarization of the atria and depolarization of the ventricles.

Moreover, many patients who suffer from congestive heart failure have hearts that still have suitable conduction, but that do not have sufficient hemodynamic results. Implantable devices have attempted to improve the hemodynamic output of such patients by providing biventricular stimulation. Others methods of improving the hemodynamics in patients that suffer from congestive heart failure are needed.

SUMMARY OF THE INVENTION

What is described herein is a device and method that dynamically adjust the AV delay and/or PV delay to improve hemodynamics.

The AV and/or PV delay of an implantable stimulation device is adjusted to cause fusion of the externally provided ventricular pacing stimuli with the patient's own natural conducted cardiac rhythm.

In one embodiment, biventricular pacing is eliminated, and a single left ventricular lead to provide all ventricular pacing. In this embodiment, a system and apparatus are provided to adjust the atrioventricular delay (i.e., the AV and/or PV delays) to achieve fusion between the left ventricular paced event and the naturally occurring R-wave.

In one embodiment, the AV/PV delay is adjusted by using morphology of the ventricular evoked response as a metric of fusion. Thus, the optimal AV and PV delays are automatically adjusted based on a servomechanism that causes fusion of the evoked response with the naturally occurring heartbeat.

The construction and method of operation of the device disclosed herein will be best understood from the following description of specific embodiments when read in connection with the accompanying drawings.

DESCRIPTION OF THE PREFERRED EMBODIMENTS

The following description includes the best mode presently contemplated for making and using the device described herein. This description is not to be taken in a limiting sense but is made merely for the purpose of describing the general principles of the device. The scope of the invention should be ascertained with reference to the issued claims. In the description that follows, like numerals or reference designators will be used to refer to like parts or elements throughout.

Figure 1:
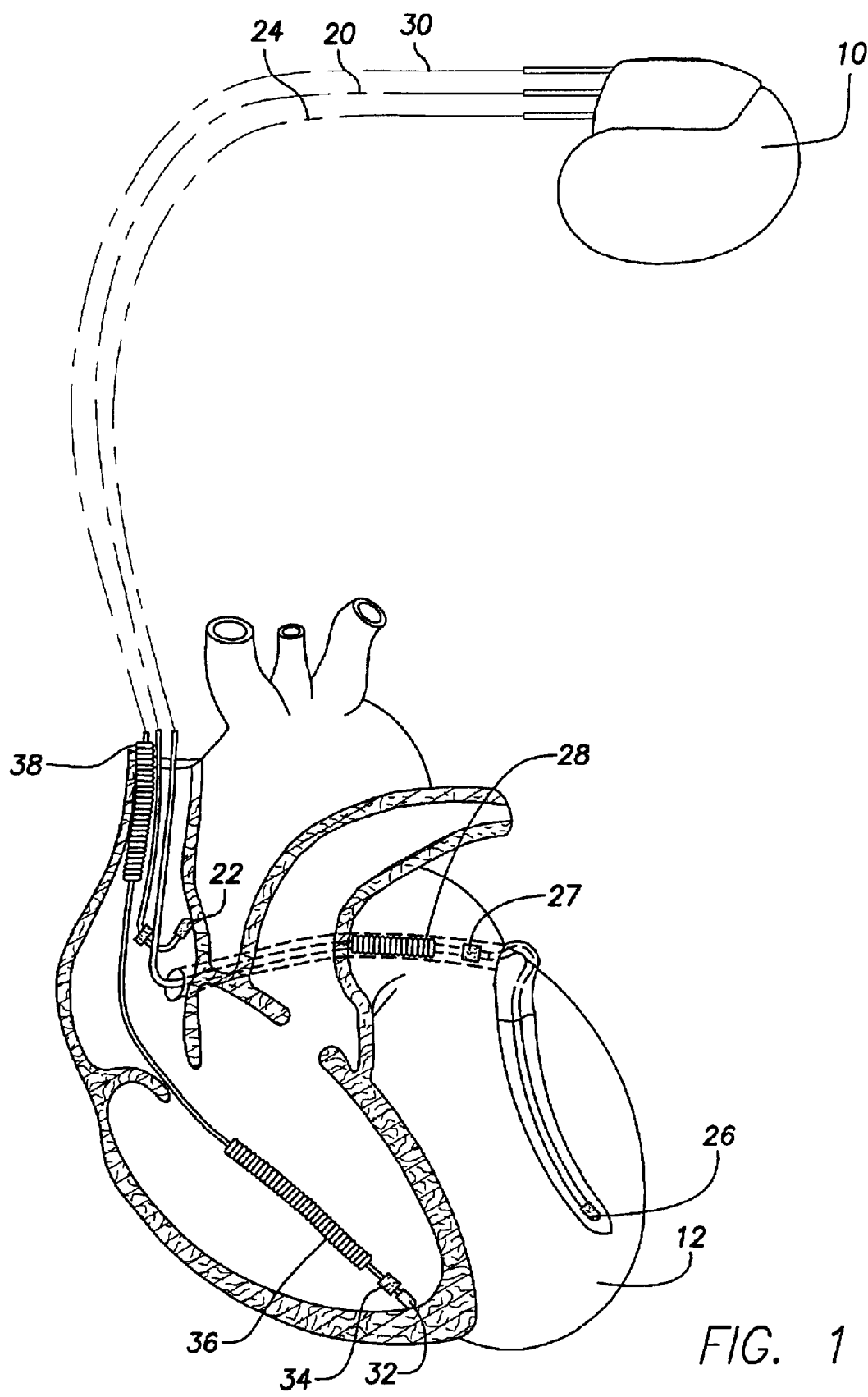
FIG. 1 is a simplified diagram illustrating an implantable stimulation device in electrical communication with at least three leads implanted into a patient's heart for delivering multi-chamber stimulation and shock therapy.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus or for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28. For a complete description of a coronary sinus lead, see U.S. patent application Ser. No. 09/457,277, filed Dec. 8, 1999, entitled "A Self-Anchoring, Steerable Coronary Sinus Lead" (Pianca et al.); and U.S. Pat. No. 5,466,254, "Coronary Sinus Lead with Atrial Sensing Capability" (Helland), which patents are hereby incorporated herein by reference.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
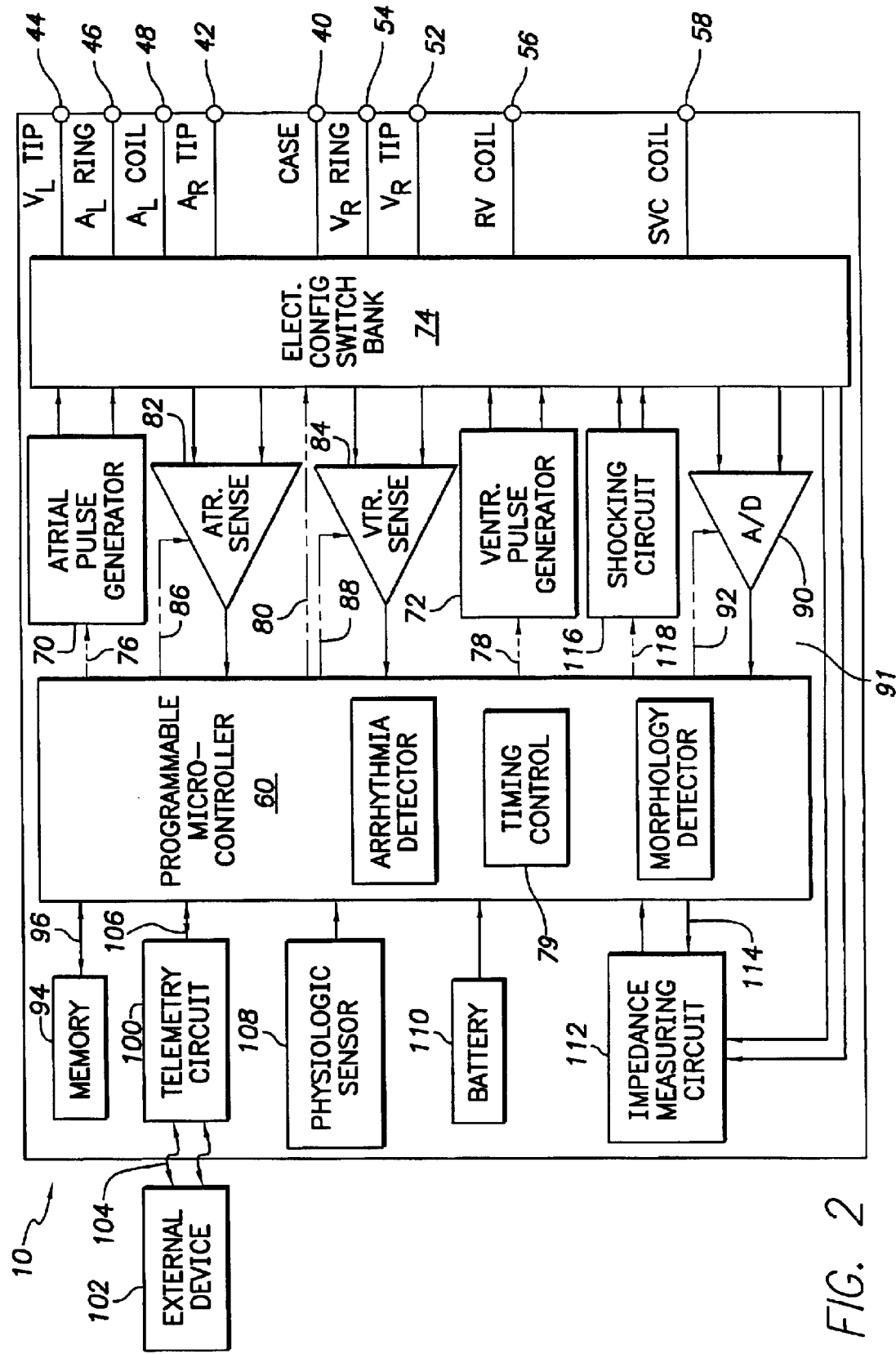
FIG. 2 is a functional block diagram of a multi-chamber implantable stimulation device illustrating the basic elements of a stimulation device, which can provide cardioversion, defibrillation and pacing stimulation in four chambers of the heart.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

Figure 16:
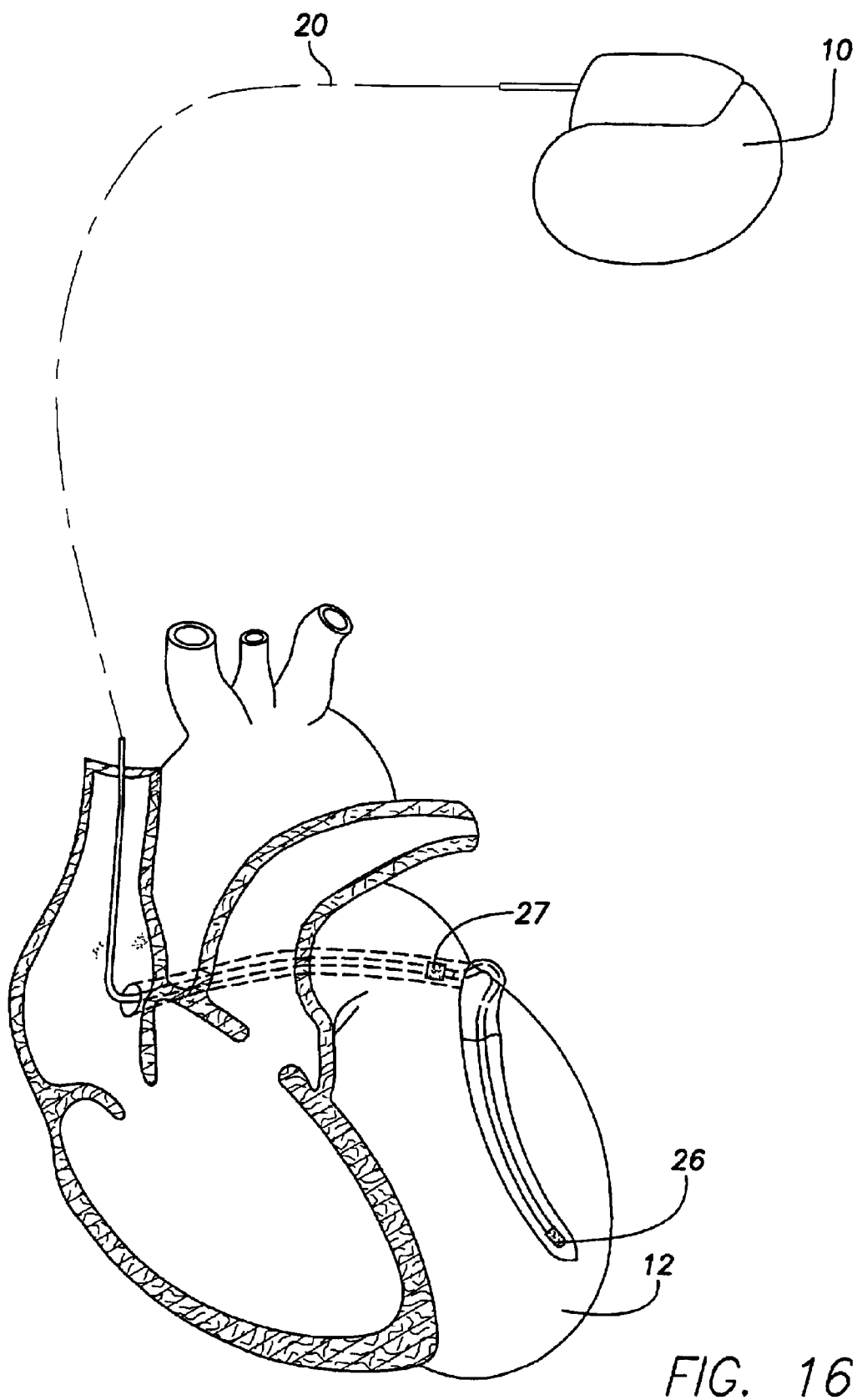
FIG. 16 is a simplified diagram illustrating an implantable stimulation device in electrical communication with only one lead implanted into a patients heart for delivering stimulation and shock therapy.

FIG. 16 shows an embodiment of an implantable stimulation device in which leads of the implantable stimulation device of FIG. 1 have been eliminated so that only one lead is implanted into a patient's heart for delivering stimulation and shock therapy.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal (AR TIP) 42 adapted for connection to the atrial tip electrode 22.

To achieve left chamber sensing, pacing and shocking, the connector includes at least a left ventricular tip terminal (VL TIP) 44, a left atrial ring terminal (AL RING) 46, and a left atrial shocking terminal (AL COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal (VR TIP) 52, a right ventricular ring terminal (VR RING) 54, a right ventricular shocking terminal (RV COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60, which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical. Rather, any suitable microcontroller 60 may be used that carries out the functions described herein. The use of microprocessor-based control circuits for performing timing and data analysis functions are well known in the art.

Representative types of control circuitry that may be used include the microprocessor-based control system of U.S. Pat. No. 4,940,052 (Mann et al.), the state-machine of U.S. Pat. No. 4,712,555 (Sholder) and U.S. Pat. No. 4,944,298 (Sholder). For a more detailed description of the various timing intervals used within the stimulation device and their interrelationship, see U.S. Pat. No. 4,788,980 (Mann et al.). The '052, '555, '298 and '980 patents are incorporated herein by reference.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity"

of the cardiac signal by selectively closing the appropriate switches, as is also known in the art. In this way, in the known art, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation.

For a complete description of a typical sensing circuit, see U.S. Pat. No. 5,573,550, entitled "Implantable Stimulation Device having a Low Noise, Low Power, Precision Amplifier for Amplifying Cardiac Signals" (Zadeh et al.). For a complete description of an automatic gain control system, see U.S. Pat. No. 5,685,315, entitled "Cardiac Arrhythmia Detection System for an Implantable Stimulation Device" (McClure et al.). Accordingly, the '550 and the '315 patents are hereby incorporated herein by reference.

The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

The sensing circuits, 82 and 84, in turn, receive control signals over signal lines, 86 and 88, from the microcontroller 60 for purposes of controlling the gain, threshold, polarization charge removal circuitry (not shown), and the timing of any blocking circuitry (not shown) coupled to the inputs of the sensing circuits, 82 and 86, as is known in the art.

For arrhythmia detection, the device 10 utilizes the atrial and ventricular sensing circuits, 82 and 84, to sense cardiac signals to determine whether a rhythm is physiologic or pathologic. As used herein sensing is reserved for the noting of an electrical signal, and "detection" is the processing of these sensed signals and noting the presence of an arrhythmia.

The timing intervals between sensed events (e.g., P-waves, R-waves, and depolarization signals associated with fibrillation which are sometimes referred to as "F-waves" or "Fibwaves" are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks, collectively referred to as "tiered therapy").

Cardiac signals are also applied to the inputs of an analog-to-digital (AND) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

Advantageously, the data acquisition system 90 may be coupled to the microcontroller, or other detection circuitry, for detecting an evoked response from the heart 12 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 60 detects a depolarization signal during a window following a stimulation pulse, the presence of which indicates that capture has occurred.

The microcontroller 60 enables capture detection by triggering the ventricular pulse generator 72 to generate a stimulation pulse, starting a capture detection window using the timing control circuitry 79 within the microcontroller 60, and enabling the data acquisition system 90 via control signal 92 to sample the cardiac signal that falls in the capture detection window and, based on the amplitude, determines if capture has occurred.

Capture detection may occur on a beat-by-beat basis or on a sampled basis. Preferably, a capture threshold search is performed once a day during at least the acute phase (e.g., the first 30 days) and less frequently thereafter. A capture threshold search would begin at a desired starting point (either a high energy level or the level at which capture is currently occurring) and decrease the energy level until capture is lost. The value at which capture is lost is known as the capture threshold. Thereafter, a safety margin is added to the capture threshold.

The implementation of capture detection circuitry and algorithms are well known. See for example, U.S. Pat. No. 4,729,376 (Decote. Jr.); U.S. Pat. No. 4,708,142 (Decote, Jr.); U.S. Pat. No. 4,686,988 (Sholder); U.S. Pat. No. 4,969,467 (Callaghan et al.); and U.S. Pat. No. 5,350,410 (Kleks et al.), which patents are hereby incorporated herein by reference. The type of capture detection system used is not critical.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, wave shape and vector of each shocking pulse to be delivered to the patient's heart 12 within each respective tier of therapy. In one embodiment, the device is able to sense and store a relatively large amount of data (e.g., from the data acquisition system 90), which data may then be used for subsequent analysis to guide the programming of the device.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106.

The telemetry circuit 100 advantageously allows intracardiac electrograms and status information relating to the operation of the device 10 (as contained in the microcontroller 60 or memory 94) to be sent to the external device 102 through an established communication link 104. For examples of such devices, see U.S. Pat. No. 4,809,697, entitled "Interactive Programming and Diagnostic System for use with Implantable Pacemaker" (Causey, Ill et al.); U.S. Pat. No. 4,944,299, entitled "High Speed Digital Telemetry System for Implantable Device" (Silvian); and U.S. patent application Ser. No. 09/223,422, filed Dec. 30, 1998, entitled "Efficient Generation of Sensing Signals in an Implantable Medical Device such as a Pacemaker or ICD" (McClure et al.) concerning a transfer of EGM data, which patents are hereby incorporated herein by reference.

In the preferred embodiment, the stimulation device 10 further includes a physiologic sensor 108, commonly referred to as a "rateresponsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V Delay, etc.) at which the atrial and ventricular pulse generators, 70 and 72, generate stimulation pulses.

While shown as being included within the stimulation device 10, it is to be understood that the physiologic sensor 108 may also be external to the stimulation device 10, yet still be implanted within or carried by the patient. A common type of rate responsive sensor is an activity sensor, such as an accelerometer or a piezoelectric crystal, which is mounted within the housing 40 of the stimulation device 10. Other types of physiologic sensors are also known, for example, sensors that sense the oxygen content of blood, respiration rate and/or minute ventilation, pH of blood, ventricular gradient, etc. However, any sensor may be used which is capable of sensing a physiological parameter that corresponds to the exercise state of the patient.

The stimulation device additionally includes a battery 110, which provides operating power to all of the circuits shown in FIG. 2. For the stimulation device 10, which employs shocking therapy, the battery 110 must be capable of operating at low current drains for long periods of time (preferably less than 10 $\mu$A), and then be capable of providing high-current pulses (for capacitor charging) when the patient requires a shock pulse (preferably, in excess of 2 A, at voltages above 2 V, for periods of 10 seconds or more). The battery 110 must also have a predictable discharge characteristic so that elective replacement time can be detected. Accordingly, the device 10 preferably employs lithium/silver vanadium oxide batteries, as is true for most (if not all) current devices.

The stimulation device 10 further includes a magnet detection circuitry (not shown), coupled to the microcontroller 60. It is the purpose of the magnet detection circuitry to detect when a magnet is placed over the stimulation device 10, which magnet may be used by a clinician to perform various test functions of the stimulation device 10 and/or to signal the microcontroller 60 that the external programmer 102 is in place to receive or transmit data to the microcontroller 60 through the telemetry circuits 100.

As further shown in FIG. 2, the device 10 is shown as having an impedance measuring circuit 112 which is enabled by the microcontroller 60 via a control signal 114. The known uses for an impedance measuring circuit 120 include, but are not limited to, lead impedance surveillance during the acute and chronic phases for proper lead positioning or dislodgment; detecting operable electrodes and automatically switching to an operable pair if dislodgment occurs; measuring respiration or minute ventilation; measuring thoracic impedance for determining shock thresholds; detecting when the device has been implanted; measuring stroke volume; and detecting the opening of heart valves, etc. The impedance measuring circuit 120 is advantageously coupled to the switch 74 so that any desired electrode may be used. The impedance measuring circuit 112 is not critical and is shown for only completeness.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118.

The shocking circuit 116 generates shocking pulses of low (up to 0.5 Joules), moderate (0.5–10 Joules), or high energy (11 to 40 Joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

According to one illustrative embodiment, the AV/PV delay of an implantable stimulation device 10 is adjusted so as to create fusion of the externally provided ventricular pacing stimuli with the patient's intrinsic ventricular depolarizations. Such a method is believed to be beneficial in treating patients that have inter-ventricular conduction defects.

In addition, this allows for the elimination of biventricular pacing, and further allows for a single left ventricular lead to provide ventricular pacing. In one embodiment, the AV/PV delay is adjusted based on the morphology of the ventricular evoked response, which is a metric of fusion. Thus, the AV and PV delays may be automatically adjusted based on a precise servomechanism to achieve fusion of the evoked response with the naturally occurring heartbeat.

It will be understood that the ventricular depolarizaton generally assumes three basic forms based upon the length of the AV/PV delay. The evoked response resulting from each of these forms is shown in FIGS. 3 to 8. FIGS. 3 to 8 are graphs that show how an evoked response changes as a function of the AV or PV delay. In these figures, the magnitude of the signal voltage is shown along the vertical axis, and time is shown along the horizontal axis.

If the AV or PV delay is relatively short, as accomplished by selecting a short AV or PV delay or by programming a negative AV/PV hysteresis within an implantable stimulation device to "on", then the ventricular evoked response is purely preemptively paced and appears as a negatively going evoked depolarization.

Figure 3:
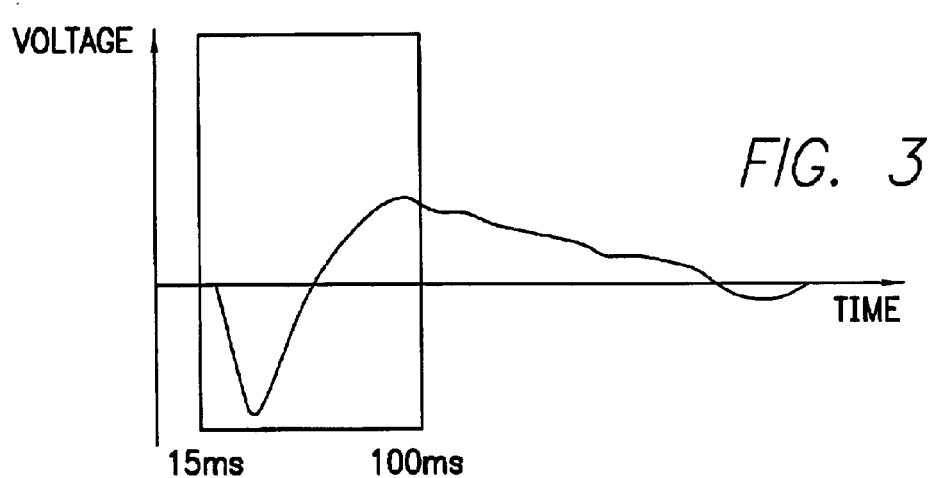
FIG. 3 is a graph illustrating an EGM curve of a fully preemptively paced evoked response.
Figure 4:
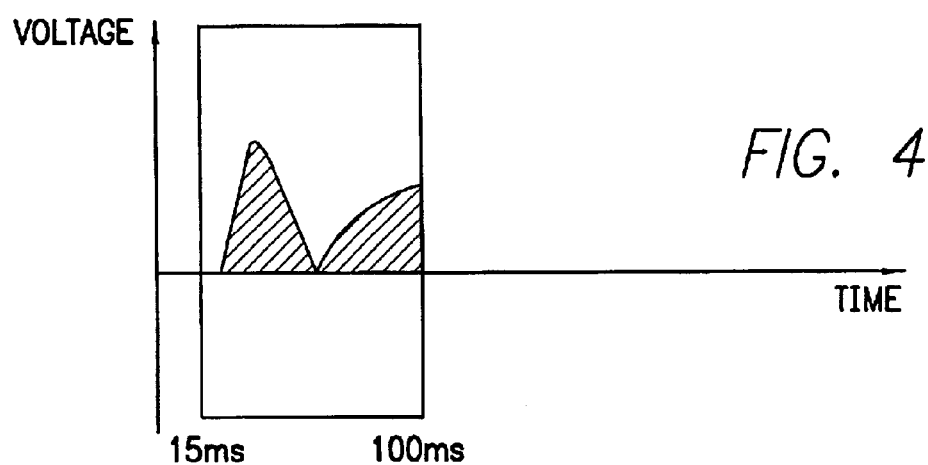
FIG. 4 is a graph illustrating the rectified EGM curve of the fully preemptively paced evoked response shown in FIG. 3 in a given time window.

FIG. 3 illustrates a typical evoked response that occurs when the ventricle is preemptively paced. The hatched area in FIG. 4 illustrates the rectified evoked response in a time window between 15 milliseconds and 100 milliseconds following a pacing pulse. The hatched area is a very good approximation of the entire evoked response signal, but it will be understood that the time window may be longer or shorter than 85 milliseconds, and may start earlier or later than 15 milliseconds after application of the ventricular stimulation. The hatched area is quite large following a fully preemptively paced event as shown and becomes much smaller with fusion.

If the AV or PV delay is long due to the selection of a long AV or PV delay or by, programming a positive AV/PV hysteresis to "on", then the ventricular depolarization is attributable to a native R-wave and the ventricular stimulus is inhibited. Even if the ventricular stimulus is delivered, the complex appears as a native R-wave would appear, because the ventricular tissue is refractory when the stimulation is applied. The depolarization appears as a negatively going depolarization or as a biphasic signal and it has morphology distinctly different from the pure preemptively paced evoked response as shown in FIG. 3.

Figure 6:
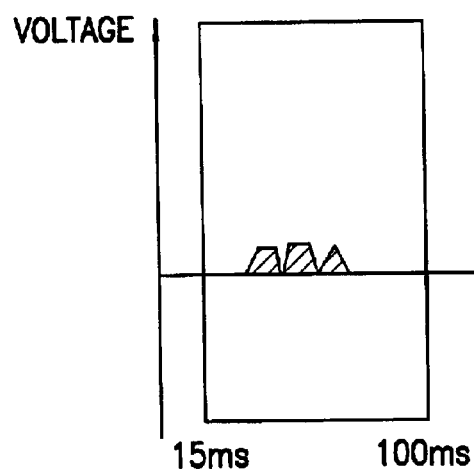
FIG. 6 is a graph illustrating the rectified EGM curve of the fully fused evoked response shown in FIG. 5 in a given time window.
Figure 7:
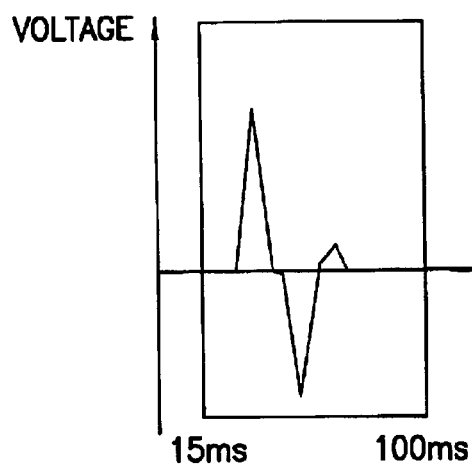
FIG. 7 is a graph illustrating an EGM curve of an evoked response with little or no fusion because the AV delay or PV delay is too long.
Figure 8:
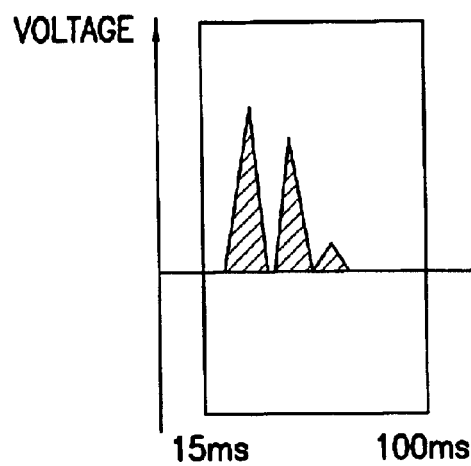
FIG. 8 is a graph illustrating the rectified EGM curve of the evoked response shown in FIG. 7 in a given time window.

FIG. 7 shows a typical cardiac response for purely intrinsic ventricular depolarization. The hatched area in FIG. 8 shows the rectified evoked response in the time window between 15 ms and 100 ms following a pacing pulse. As stated, the hatched area is a very good approximation of the evoked response signal. It will be apparent that the area defined by the curve in FIG. 8 is larger than the area for the signal shown in FIG. 6.

Finally, when the AV or PV delay is adjusted so that the stimulation pulse is delivered concurrently or almost concurrently with an intrinsic depolarization, the detected evoked response appears to significantly diminish in amplitude. This is caused by fusion of the stimulation pulse with the intrinsic R-wave.

Figure 5:
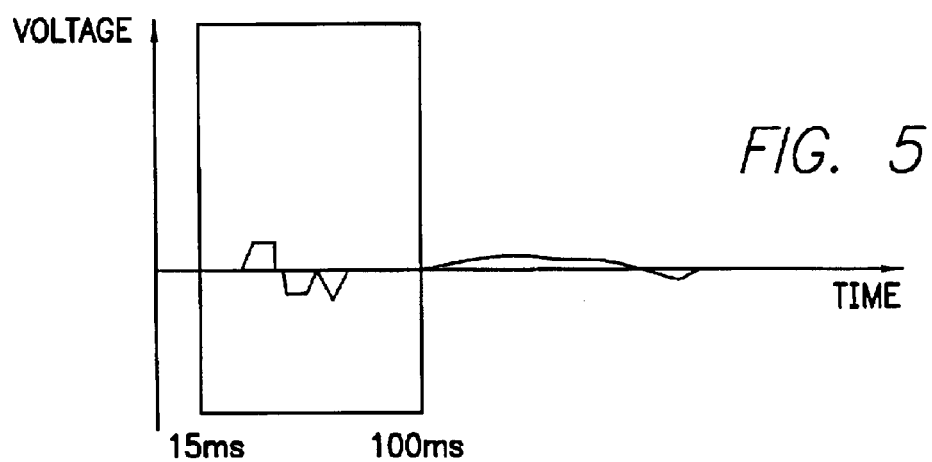
FIG. 5 is a graph illustrating an EGM curve of a fully fused evoked response.

FIGS. 5 and 6 demonstrate a typical fusion beat. In FIG. 5 the sensed depolarization voltage is very small due to wave front cancellation resulting from the fusion beat. The trace of FIG. 5 may be used as a target fusion response (e.g., a template) that is achieved with properly timed AV and PV delays.

The hatched area in FIG. 6 shows the rectified evoked response in a time window between 15 ms and 100 ms following a pacing pulse. As stated above, peak amplitude of the hatched area is a very good criterion for detecting fusion. The amplitude of the signal in the hatched area in FIG. 6 is relatively small due to fusion. This is desirable and indicates an operation at or near the ideal AV or PV delay.

While peak amplitude is mentioned as one criterion for detecting a fusion beat, it is well known in the art that other criteria may be monitored. For example, the maximum slope of a positive- or negative-going signal, the integral of the signal, or some form of template matching can all be used to distinguish between fusion and non-fusion beats.

FIGS. 9 to 12 show graphs that describe exemplary (or expected) measurement data for various PV delays. The vertical axis indicates a voltage potential and the horizontal axis indicates time. Each of FIGS. 9 to 12 include both the measured EGM curve and, above that, the absolute value of the measured EGM curve, i.e. the rectified EGM curve.

Figure 9:
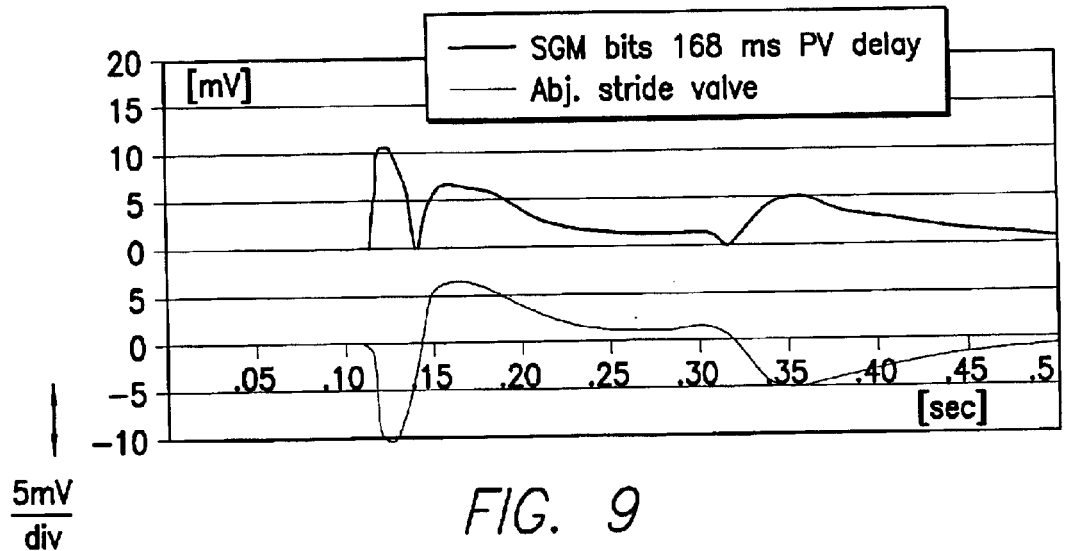
FIG. 9 is a graph illustrating a measured EGM curve and its absolute value for a PV delay of 130 milliseconds.

FIG. 9 shows a measured EGM curve and its absolute value for a PV delay of 130 milliseconds. As can be seen, the integral of the rectified EGM curve is substantially larger than in FIGS. 10 and 11. FIG. 9 corresponds to depolarization that results solely from an applied stimulation pulse.

Figure 10:
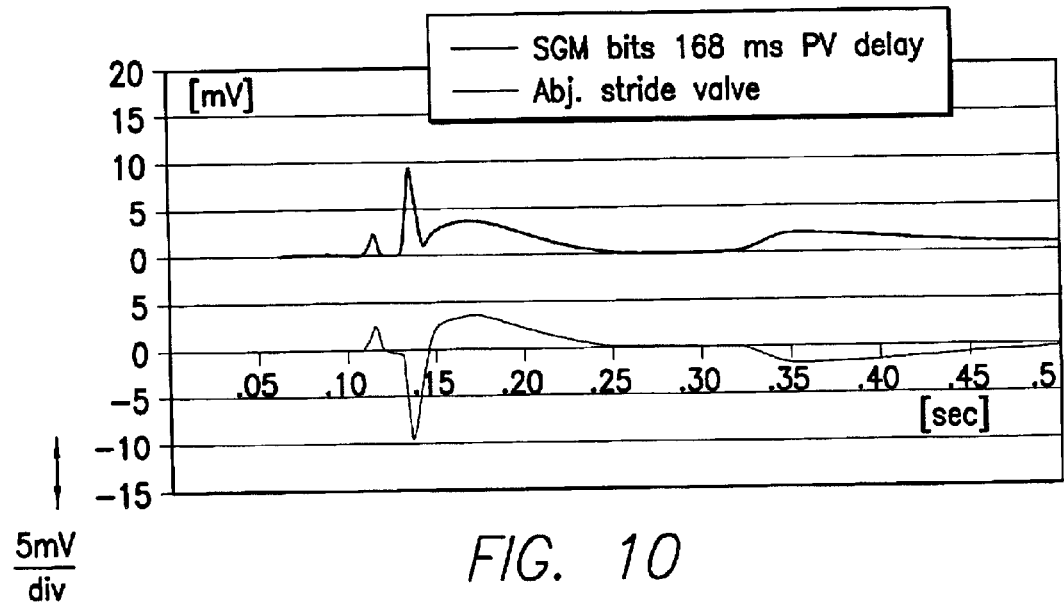
FIG. 10 is a graph illustrating a measured EGM curve and its absolute value for a PV delay of 140 milliseconds.

FIG. 10 shows a measured EGM curve and its absolute value for a PV delay of 140 milliseconds. The integral of the rectified EGM curve decreases with an increasing PV delay until a PV delay of 150 milliseconds, and corresponds to a pseudofusion beat.

Figure 11:
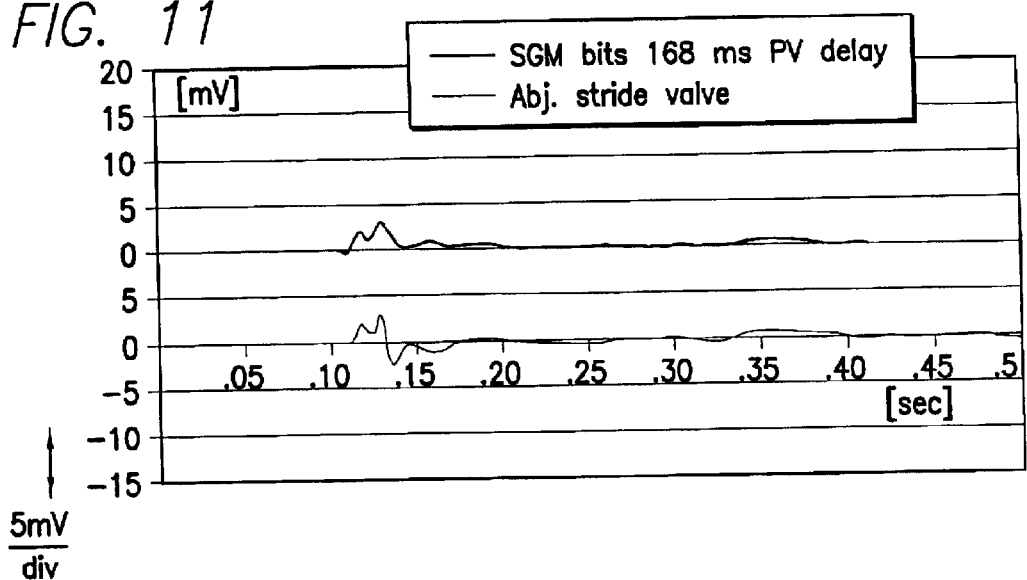
FIG. 11 is a graph illustrating a measured EGM curve and its absolute value for a PV delay of 150 milliseconds.

FIG. 11 shows the measured EGM curve for a PV delay of 150 milliseconds. At a PV delay of 150 milliseconds, the integral of the EGM curve reaches a minimum and increases again with further increasing of PV delays. This EGM curve corresponds to a fusion beat.

Figure 12:
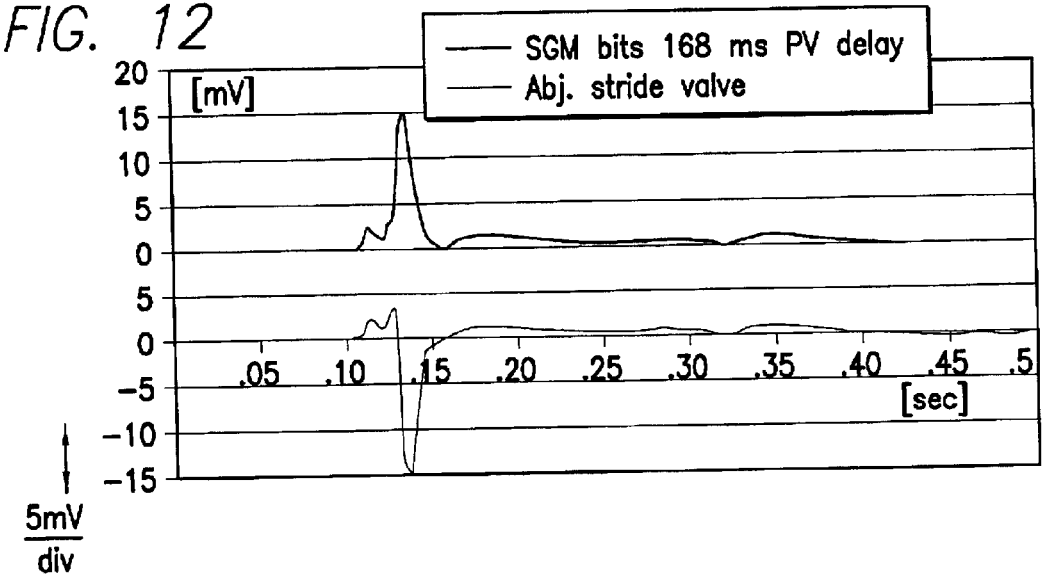
FIG. 12 is a graph illustrating a measured EGM curve and its absolute value for a PV delay of 160 milliseconds.

FIG. 12 shows a measured EGM curve and its absolute value for a PV delay of 160 milliseconds. This evoked response corresponds to depolarization resulting solely from intrinsic depolarization.

Therefore, it will be apparent that FIG. 11, corresponding to a delay of 150 ms, is the preferred delay for achieving fusion. Because patients differ, test results may produce various ideal delay times for different patients.

Figure 13:
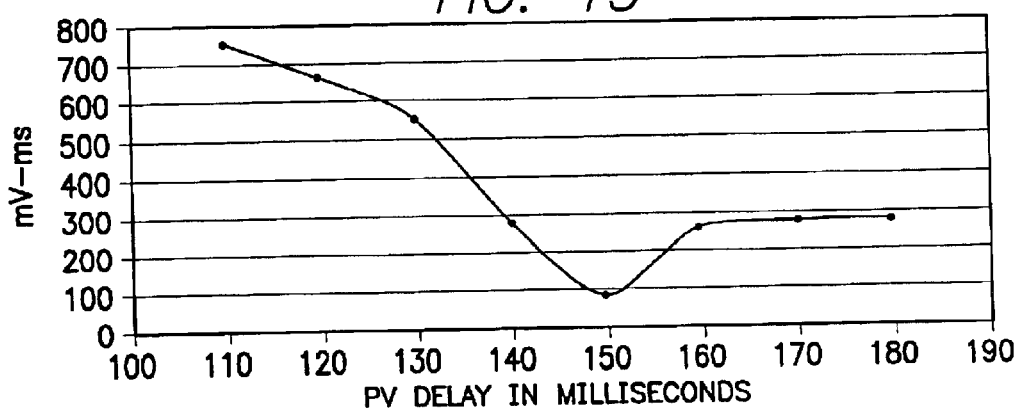
FIG. 13 is a graph illustrating the integral of the rectified EGM curves versus the PV delay.

FIG. 13 is a graph showing how the integral of the absolute value of the EGM curves changes as the PV delay is altered. FIG. 13 is based on data collected from the results in FIGS. 9 to 12. For short PV delays (e.g., in the range of 110 milliseconds to 150 milliseconds), the integral value decreases with increasing PV delays. For a PV delay of 150 milliseconds, the integral of the absolute value of EGM curve has a minimum. For longer PV delays above 150 milliseconds, the integral value increases with increasing PV delays.

It will be understood that the integral values are influenced by the electrode type. In one embodiment, the electrodes used have low polarization properties. Low polarization electrodes typically have little or no voltage transient due to charging of the Helmholtz layer following a stimulation pulse. This charging of the Helmholtz layer results in a voltage transient that in an extreme may obscure the evoked response waveform. The problem is well known to those skilled in the art and is overcome by using electrodes that are coated with platinum black, TiN, Iridium, Oxide, or made with activated vitreous carbon.

It is also understood that the stimulation pulses need to be in excess of the stimulation threshold in order to stimulate the tissue and cause an evoked response. If the clinician manually sets the output, the programmed output stimulus magnitude is normally set to two times the minimal stimulus amplitude required to achieve capture. This provides a safety margin to assure capture even as thresholds change throughout the day or in response to drug changes and/or the overall health of the patient. Alternatively, devices may have automatic output regulation systems that maintain capture automatically by verifying the presence of an evoked response. Such automatic output regulation systems are also well known to those familiar with the art.

The terms long PV delay and short PV delay are not defined in terms of absolute values but are to be understood as delays measured with respect to the minimum of a curve as shown in FIG. 13. The minimum of the curve in FIG. 13 may be different for different physiological conditions, different patients etc.

Figure 14:
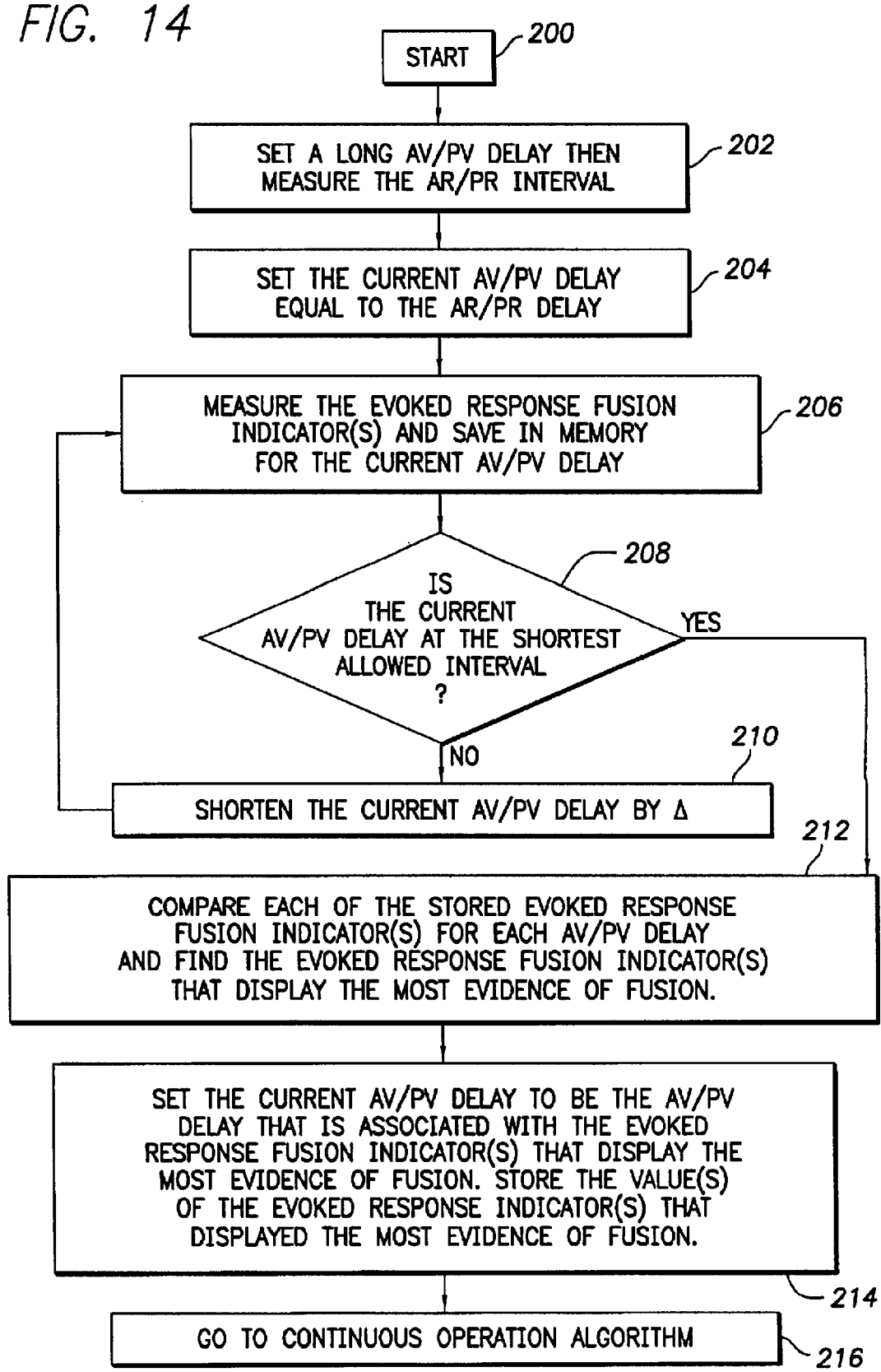
FIG. 14 is a flow chart diagram describing an overview of the operation of an embodiment.
Figure 15:
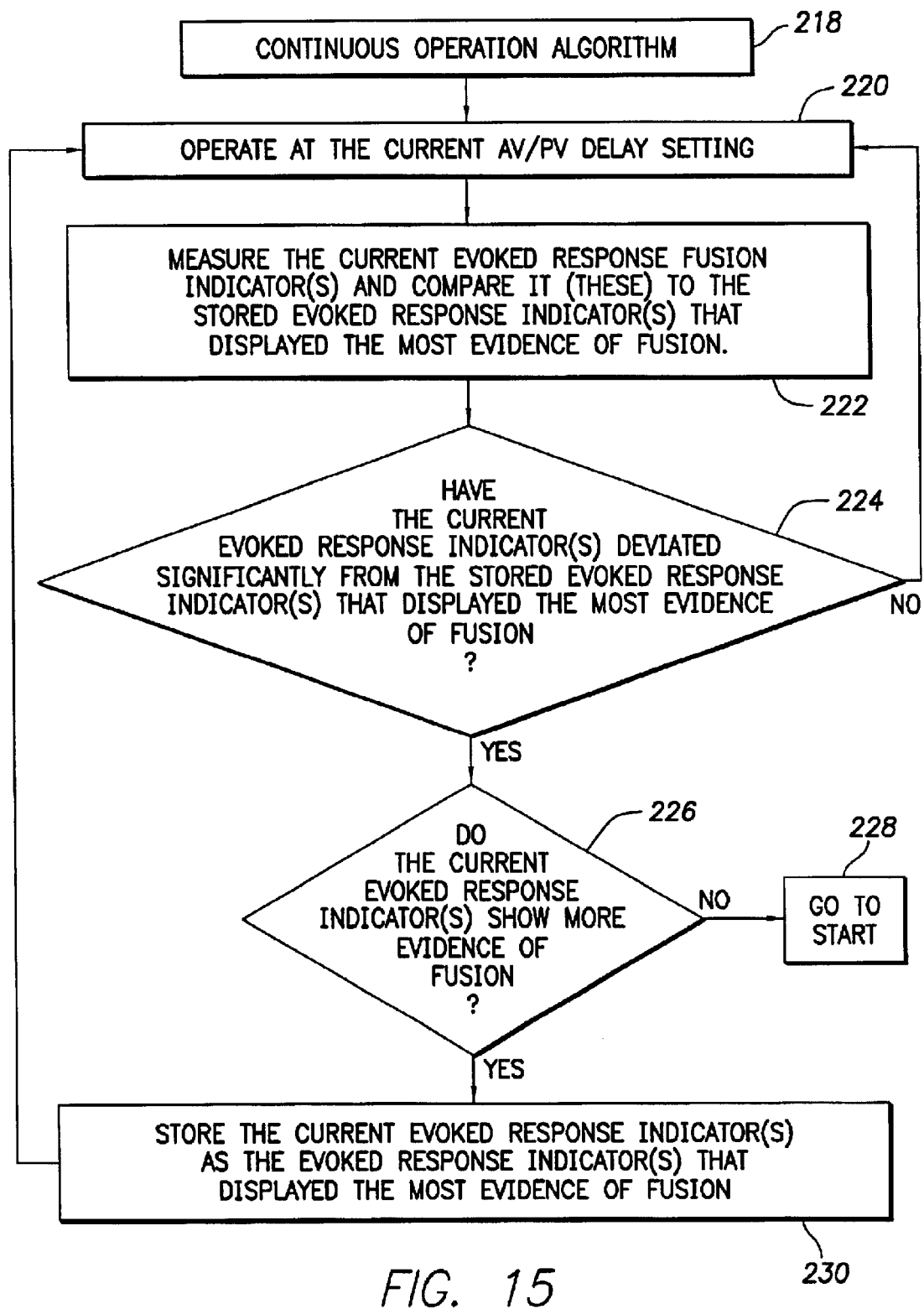
FIG. 15 is a flow chart diagram describing an overview of the operation of an embodiment.

In FIGS. 14 and 15, flow charts are shown describing an overview of the operation of one embodiment of a device that is operative to adjust an atrioventrcular delay (AV and/or PV delay) to achieve fusion.

In these flow charts, the various algorithmic steps are summarized in individual "blocks". Such blocks describe specific actions or decisions that are carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

As shown in FIG. 14, after the start of the operation (block 200), first a long AV/PV delay is set (block 202). A long AV/PV delay may, for example, be a delay of greater than about 180 milliseconds depending on the patient particular patient's characteristics. The long AV/PV delay may be based on patient-specific data that was previously acquired, or may alternatively be a default value based on generic patient information.

After setting the long AV/PV delay, the AR/PR interval is measured (block 202). In a following step (block 204), the current AV/PV delay is set to be equal to the AR/PR delay. After the AV/PV delay is set to be equal to the AR/PR delay, the evoked response fusion indicators are measured (block 206). Such evoked responses are shown in an exemplary manner in FIGS. 3, 5, and 7. The indicators may be, for example, the peak amplitude of the evoked response, the integral value, the value of the integral of the absolute value of the evoked response, the maximum slope of the positive- or negative-going signal, or samples of the signal in the time window.

The evoked response data is then saved in memory of the stimulation device 10 and associated with the current AV/PV delay. Next a determination is made whether the current AV/PV delay is at the shortest allowed interval (block 208).

If the AV/PV delay is longer than the shortest allowed delay, then the current AV/PV delay is shortened by a predefined incremental value A (block 210). Once the AV/PV delay is shortened, the evoked response fusion indicators are measured again, this time for the new (shortened) AV/PV delay (block 206). The steps of shortening the AV/PV delay and measuring the evoked response fusion indicators are repeated until the current AV/PV delay is at the shortest allowed interval.

It will be apparent to those skilled in the art that one or more measurements can be taken at AV/PV delays that are longer than the AR/PR delay values.

Once the fusion indicators of the evoked response have been measured and stored for all AV/PV delays, the evoked response data stored in the memory device of the stimulation device 10 is processed to determine which of the evoked responses displays the most evidence of fusion (block 212). In one embodiment, the integral values for the respective evoked responses are processed to determine an AV and/or PV delay that results in the lowest integral value. The integral values can be plotted as shown in FIG. 13, with a best-fit curve applied to determine an ideal AV/PV delay, or alternately the actual AV/PV delay value tested that resulted in the lowest integral value may be chosen as the ideal AV/PV delay value.

As shown in FIGS. 3 to 8, fusion may be determined by comparing the integral values of rectified evoked responses in a given time window. After the evoked response fusion indicators have been compared, the current AV/PV delay is set to be the AV/PV delay that is associated with the evoked response fusion indicators that display the most evidence of fusion.

In one embodiment, of the data corresponding to the evoked response that displayed the most evidence of fusion is then stored in the memory of the stimulation device 10 (step 214). Then a continuous operation algorithm is called up (step 216).

FIG. 15 illustrates the method steps that are performed after calling up the continuous operation algorithm (block 218). As the stimulation device 10 is operated at the current AV/PV delay setting (block 220), the current evoked response fusion indicators are measured and compared to the stored evoked response indicators that had shown the most evidence of fusion (block 222). It will be understood that this can be done continuously or periodically (e.g., once per minute, once per hour, etc.).

A decision is made as to whether the current evoked response indicators deviate significantly from the stored evoked response indicators that had shown the most evidence of fusion (block 224). If the current evoked response has not significantly deviated from the stored evoked response indicators with the most evidence of fusion, then the stimulation device 10 continues operating at the AV/PV delay setting that had previously been set (see block 214). However, if the current evoked response indicators deviated significantly from the stored evoked response indicators that displayed the most evidence of fusion (block 224), then a decision (block 226) is made as to whether the current evoked response indicators display more evidence of fusion than the stored evoked response indicators that had been determined in blocks 206 to 212.

If the interrogation in block 226 indicates that the current evoked response indicators do not show more evidence of fusion, then the program goes through block 228 back to start (block 200) and the measurement, storage and comparison process begins again. On the other hand, if the interrogation in block 226 has the result, that the current evoked response indicators show more evidence of fusion, then the current evoked response indicators are stored as the (new) evoked response indicators that displayed the most evidence of fusion (block 230) and the program continues with block 220 and the stimulation device 10 operates at the current AV/PV delay.

FIG. 16 shows one embodiment of a stimulation device 10 that is programmed to carry out the algorithm shown in FIGS. 14 and 15. The stimulation device 10 has one lead 24 with two electrodes, namely the left ventricular tip electrode 26 and the left atrial ring electrode 27, which are respectively used for sensing and stimulating the atrium and ventricle. It will be understood that lead 24 can have more than two electrodes for sensing and/or stimulating.

The electrode 27 is placed in the coronary sinus region (i.e., either in the coronary sinus itself or in a vein connected to the coronary sinus, as is well known in the art) and is used to stimulate and sense the left ventricle of the heart 12. The stimulation device shown in FIG. 16 has the advantage that only one lead is required, yet it achieves stimulation by fusing the signals from the LV stimulus with the conducted RV event. Only two electrodes are used, one to stimulate and sense the left ventricle and the other to stimulate either the right or left atrium as the lead passes through the coronary sinus to the left ventricle.

An alternate embodiment of the stimulation device includes both a right and left ventricular lead as shown in FIG. 1. In this embodiment, the right ventricular stimulus and the left ventricular stimulus are both set so as to cause fusion with the intrinsic depolarizations.

This mode of operation uses three loci of excitation. These three loci of excitation are achieved by using optimal AVR or PVR delays that fuse optimally with the intrinsic right ventricular event and by using AVL or PVL delays to fuse with the intrinsic left ventricular event. In this embodiment the conducted beat can originate from either intrinsic atrial depolarizations or paced atrial depolarizations that conduct through the AV node. Setting the atrioventricular delays for both the right ventricle and for the left ventricle can be achieved in various ways. In one embodiment, a first ventricle is not stimulated while the atrioventricular delay that results in fusion is determined for the second ventricle. Once that delay is set, operation is reversed, and the second ventricle is not stimulated while the appropriate atrioventricular delay is determined for the first ventricle. Once the respective delays are determined, the ventricles are stimulated at the respective atrioventricular delays to achieve fusion in both the left and right ventricles.

In another embodiment, the appropriate atrioventricular delay is determined for the first ventricle, and then the first ventricle is paced at the determined atrioventricular delay while an appropriate atrioventricular delay is determined for the second ventricle. Then, both ventricles are paced at the respective atrioventricular delays.

In one embodiment, the once the ideal $AV_R$ or $PV_R$ delays and/or $AV_L$ or $PV_L$ delays are determined as described above in connection with FIGS. 14 and 15, the delays may be further adjusted by slightly shortening the respective delays (e.g., on the order of 10–50 milliseconds, preferably about 20–30 milliseconds). This shortening takes into account potential delays in sensing an intrinsic ventricular event (e.g., due to electrode placement, etc.), and may lead to even more optimal fusion between the intrinsic event and the applied stimulation.

From the foregoing, it will be apparent that what is described is a device and method that automatically adjust an atrioventricular delay to achieve fusion with an intrinsic ventricular event. This results in a superposition of the stimulation and the intrinsic activity, which can improve hemodynamics.

What is claimed is:

1. A method of setting an atrioventricular delay between an atrial event and stimulation of a ventricle, the method comprising:
   providing stimulation pulses to the ventricle at a plurality of different atrioventricular delays after respective atrial events;
   acquiring electrical heart activity data resulting from the applied stimulation pulses;
   processing the electrical heart activity data to determine an atrioventricular delay that results in a fusion beat; and
   setting an atrioventricular delay value to a particular value based on the atrioventricular delay so as to achieve fusion;
   wherein processing the electrical heart activity comprises comparing at least one parameter from each set of data to determine which of the sets displays the strongest degree of fusion.

2. The method of claim 1, wherein processing the electrical heart activity comprises calculating an integral of an evoked response from each set of data.

3. The method of claim 1, wherein processing the electrical heart activity comprises calculating a peak amplitude of an evoked response from each set of data.

4. The method of claim 3, further comprising defining at least one threshold value, and comparing the respective peak amplitudes with the threshold.

5. The method of claim 1, wherein processing the electrical heart activity comprises comparing each set of data with a stored set of fusion data to determine which of the sets displays the strongest degree of fusion.

6. The method of claim 1, wherein acquiring the electrical heart activity comprises acquiring a signal corresponding to an evoked response for each stimulation pulse provided.

7. The method of claim 1, wherein processing the electrical heart activity comprises comparing a parameter of each set of data with a threshold value.

8. The method of claim 7, wherein comparing a parameter comprises comparing a peak amplitude for each set of data.

9. The method of claim 8, wherein comparing a peak amplitude comprises comparing each peak amplitude with an upper and lower threshold value, and wherein setting the atrioventricular delay value comprises setting the atrioventricular delay value to a value that falls between the respective threshold values.

10. The method of claim 1, wherein providing the stimulation pulses comprises providing the stimulation pulses at each of a plurality of atrioventricular delays after intrinsic atrial depolarizations.

11. The method of claim 1, wherein providing the stimulation pulses comprises providing the stimulation pulses at each of a plurality of atrioventricular delays after paced atrial depolarizations.

12. The method of claim 1, wherein setting the atrioventricular delay value comprises setting the atrioventricular delay value to the delay that resulted in a fusion beat.

13. The method of claim 1, wherein setting the atrioventricular delay value comprises setting the atrioventricular delay value to a value that is a predetermined amount shorter than the delay that resulted in a fusion beat.

14. The method of claim 13, wherein the atrioventricular delay value is between about 10 and about 50 milliseconds shorter than the atrioventricular delay that resulted in a fusion beat.

15. A method of setting an atrioventricular delay between an atrial event and stimulation of a ventride, the method comprising:
   adjusting the atrioventricular delay until an evoked response from the ventricle indicates a fusion beat;
   comparing at least one parameter from each evoked response to determine which of the evoked responses displays the strongest degree of fusion; and
   setting the atrioventricular delay to a value based on the atrioventicular delay that results in the strongest degree of fusion so as to achieve fusion.

16. The method of claim 15, wherein comparing at least one parameter comprises calculating an integral of each evoked response.

17. The method of claim 15, wherein comparing at least one parameter comprises calculating a peak amplitude of each evoked response.

18. The method of claim 15, further comprising defining at least one threshold value, and comparing a parameter value of each evoked response with the threshold value.

19. The method of claim 15, further comprising comparing each evoked response with a stored set of fusion data to determine which of the sets displays the strongest degree of fusion.

20. The method of claim 15, wherein setting the atrioventricular delay value comprises setting the atrioventricular delay value to a value that is a predetermined amount shorter than the delay that resulted in a fusion beat.

21. The method of claim 20, wherein the atrioventricular delay value is between about 10 and about 50 milliseconds shorter than the atrioventricular delay that resulted in a fusion beat.

22. A system for setting an atrioventricular delay between an atrial event and stimulation of a ventricle, the system comprising:
   a stimulation generator that is operative to generate stimulation pulses to be delivered to the ventricle;
   circuitry in communication with the stimulation generator, the circuitry being operative to control the stimulation generator to produce stimulation pulses at a plurality of different atrioventricular delays after respective atrial events;

a sensor that is operative to acquire electrical heart activity data resulting from the applied stimulation pulses;

wherein the circuitry is in communication with the sensor and is operative to process the electrical heart activity data to determine an atrioventricular delay that results in a fusion beat, wherein processing the electrical heart activity data comprises comparing at least one parameter from each set of data to determine which of the sets displays the strongest degree of fusion, and wherein the circuitry is operative to set the atrioventricular delay value to a value based on the atrioventricular delay that results in the strongest degree of fusion so as to achieve fusion.

23. The system of claim 22 wherein the circuitry is operative to set the atrioventricular delay to a value that is a predetermined amount below the value of the delay that results in the fusion beat.

24. The system of claim 22 wherein the circuitry comprises a programmed controller.

25. The system of claim 22 wherein the circuitry is operative to calculate at least one of an integral value, peak amplitude value, and maximum slope for the data collected at each atrioventricular delay.

26. A method of setting at least one of an AV delay and a PV delay in an implantable stimulation device, wherein the method comprises acquiring evoked response data for a plurality of delays for at least one of AV delays and PV delays;

comparing the data and determining a given one of the delays whose data displays the most evidence of fusion; and setting a current delay to the delay that displayed the most evidence of fusion;

wherein comparing the data comprises comparing integral values of evoked responses with one another and determining the delay displaying the most evidence of fusion by finding a smallest one of the integral values.

27. The method according to claim 26, further comprising storing data relating to the delay that displayed the most evidence of fusion.

28. A method of biventricular pacing comprising:

providing stimulation pulses to a right ventricle at a plurality of different atrioventricular delays after respective sensed events in the right atrium;

providing stimulation pulses to a left ventricle at a plurality of different atrioventricular delays after respective sensed events in the left atrium;

acquiring electrical heart activity data resulting from the applied stimulation pulses;

processing the electrical heart activity data to determine atrioventricular delays that result in fusion beats in the right and left ventricles; and setting a left atrioventricular delay value and a right atrioventricular delay value to particular values based on the respective atrioventricular delays so as to achieve fusion in the left and right ventricles.

29. The method of claim 28, wherein processing the electrical heart activity comprises comparing at least one parameter from each set of data to determine which set displays the strongest degree of fusion in the left ventricle and the right ventricle.

30. The method of claim 29, wherein processing the electrical heart activity comprises calculating an integral of an evoked response from each set of data.

31. The method of claim 29, wherein processing the electrical heart activity comprises calculating a peak amplitude of an evoked response from each set of data.

32. The method of claim 29, further comprising defining at least one threshold value, and comparing the respective peak amplitudes with the threshold.

33. The method of claim 29, wherein processing the electrical heart activity comprises comparing each set of data with a stored set of fusion data to determine which of the sets displays the strongest degree of fusion for the right ventricle and for the left ventricle.

34. The method of claim 29, wherein comparing a parameter comprises comparing a peak amplitude for each set of data.

35. The method of claim 28, wherein setting the atrioventricular delay values comprises setting the atrioventricular delay values to the delays that resulted in fusion beats in the right and left ventricles.

36. The method of claim 28, wherein setting the atrioventricular delay values comprises setting the atrioventricular delay values to respective values that are a predetermined amount shorter than the delays that resulted in fusion beats in the right and left ventricles.

37. The method of claim 36, wherein the atrioventricular delay values are between about 10 and about 50 milliseconds shorter than the atrioventricular delays that resulted in fusion beats in the right and left ventricles.

* * * * *